(12) United States Patent
Schroder et al.

(10) Patent No.: US 6,422,068 B1
(45) Date of Patent: Jul. 23, 2002

(54) TEST RIG AND PARTICULATE DEPOSIT AND CLEANING EVALUATION PROCESSES USING THE SAME

(75) Inventors: Mark Stewart Schroder, Hendersonville, NC (US); Donald Ernest Woodmansee, Schenectady, NY (US); Douglas Frank Beadie, Greer, SC (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/675,655

(22) Filed: Sep. 29, 2000

(51) Int. Cl.[7] ............................................... G01N 15/06
(52) U.S. Cl. ......................................... 73/61.71; 73/38
(58) Field of Search ............................. 73/61.71, 61.72, 73/61.73, 61.62, 61.63, 38, 865.5

(56) References Cited

U.S. PATENT DOCUMENTS

| | | | | |
|---|---|---|---|---|
| 2,617,719 A | * | 11/1952 | Stewart | 23/312 |
| 3,499,315 A | * | 3/1970 | Marino | 73/61 |
| 3,659,940 A | * | 5/1972 | Hansen et al. | 356/36 |
| 5,086,646 A | * | 2/1992 | Janison et al. | 73/65 |
| 5,095,740 A | * | 3/1992 | Hodgson et al. | 73/61 R |
| 5,329,807 A | * | 7/1994 | Sugar et al. | 73/40 |
| 5,731,513 A | * | 3/1998 | Bull | 73/61.66 |
| 6,230,551 B1 | * | 5/2001 | Burniston | 73/61.73 |

\* cited by examiner

*Primary Examiner*—Hezron Williams
*Assistant Examiner*—Charles D. Garber
(74) *Attorney, Agent, or Firm*—Nixon & Vanderhye PC

(57) ABSTRACT

A rig and test program for determining the amount, if any, of contamination that will collect in the passages of a fluid flow system, such as a power plant fluid delivery system to equipment assemblies or sub-assemblies, and for establishing methods and processes for removing contamination therefrom. In the presently proposed embodiment, the rig and test programs are adapted in particular to utilize a high-pressure, high-volume water flush to remove contamination from substantially the entire fluid delivery system, both the quantity of contamination and as disposed or deposited within the system.

23 Claims, 2 Drawing Sheets

TEST RIG AND PARTICULATE DEPOSIT AND CLEANING EVALUATION PROCESSES USING THE SAME

This invention was made with Government support under Government contract No. DE-FC21-95-MC31176 awarded by the Department of Energy. The Government has certain rights in this invention.

BACKGROUND OF THE INVENTION

The present invention relates to a rig for determining the amount of contamination that will collect in the passages within power plant components and for establishing removal methods and processes for removing contamination via a water flushing technique.

Particulate contamination is a well-known source of mechanical system failures. Particulates can cause abrasion at the interface between moving parts and contamination of fluids flowing through the system, erode structures in high velocity fluid flow paths, and/or create deposits that either reduce desired flows or insulate against desired heat transfer. There is an interest, therefore, in ensuring that parts incorporated in mechanical systems, exhibit a certain level of surface cleanliness to minimize the potential for debris accumulation during system operation. There is also an interest in providing procedures by which isolated components or assembled components can be cleaned before or after installation so as to remove particulate contamination.

For example, in certain power generating systems, steam-born magnetite (iron oxide) from the plant heat recovery steam generator (HRSG), especially from the super heater, is expected to deposit in certain portions of the system. Gas turbine engines can be designed with protections in place in both assembly and operation to keep particulate deposition rates in important areas low so that deposits will not substantially limit system efficiency or component life. To establish suitable protections it must be determined if loose or loosely adhered solid contaminates will become trapped within, hardware of the machine. Even after cleanliness protocols have been established for both assembly and operation to keep particulate deposition rates in critical areas sufficiently low, a procedure for removing particulate contamination without engine disassembly would enhance engine availability.

The prior art for cleaning power plant circuits is well-established, using a number of chemical cleaning processes, i.e., pickling oxides with acid and complexing agents, followed by thorough plant rinsing. Such processes have been generally satisfactory where the steam circuits are fabricating by welding. In some systems, however, many of the internal joints must be assembled and disassembled using interference joints, many of which are designed to handle the small but necessary relative motion of components. These interference joints are not amenable to the usual chemical cleaning because their long narrow gaps will hold the chemicals in spite of repeated rinsing. In addition, the feed of these aggressive liquids across labyrinth gas seals on the rotor supply coupling would create an unmanageable chemical collection problem compared to boilers.

BRIEF SUMMARY OF THE INVENTION

As noted above, cleanliness is of importance to mechanical systems, including power plant components. Accordingly, the invention was developed to quantify and verify particulate contamination abatement procedures such as flushing. More particularly, the invention provides a rig and test program to determine the amount, if any, of contamination that will collect in the passages of a fluid flow system, and to establish methods and processes for removing contamination therefrom. The invention is described hereinbelow with reference to its exemplary use for evaluating debris accumulation and a method for cleaning power plant components. However, the invention is not limited to the evaluation of such specified critical components, nor to the presently preferred flush cleaning process described hereinbelow.

According to a preferred embodiment, the rig is designed so as to be representative of a power plant fluid delivery system and is capable of simulating, e.g., $1/60^{th}$ scale of the actual hardware. In the presently proposed embodiment, the rig and test program are adapted in particular to determine if a high-pressure, high-volume water flush can remove contamination from substantially an entire assembly or sub-assembly and its fluid delivery system; both the quantity of contamination and as disposed or deposited within the system.

Water flushing is a cleaning method that is routinely used in many different applications. The main feature of the rig of the invention, however, is its flexible design configuration which is capable of a wide variety of volumetric flows and which is characterized in that it may be used in any component or assembly cleaning evaluation. Moreover, the invention is sufficiently adaptable to be used as a final system wide cleaning operation for power plant equipment. Thus, the invention was developed to verify methods for cleaning power plant components and in particular to provide a scale model, such as a $1/6^{th}$ scale model, flushing rig to test the success of contamination removal by way of high pressure and volume water flush. By using such a scale model rig, the feasibility of cleaning an entire fluid delivery system and its components by scaling up to the entire system can be achieved in the field prior to power plant completion.

BRIEF DESCRIPTION OF THE DRAWINGS

These, as well as other objects and advantages of this invention, will be more completely understood and appreciated by careful study of the following more detailed description of the presently preferred exemplary embodiments of the invention taken in conjunction with the accompanying drawings, in which.

DETAILED DESCRIPTION OF THE INVENTION

Figure 1:
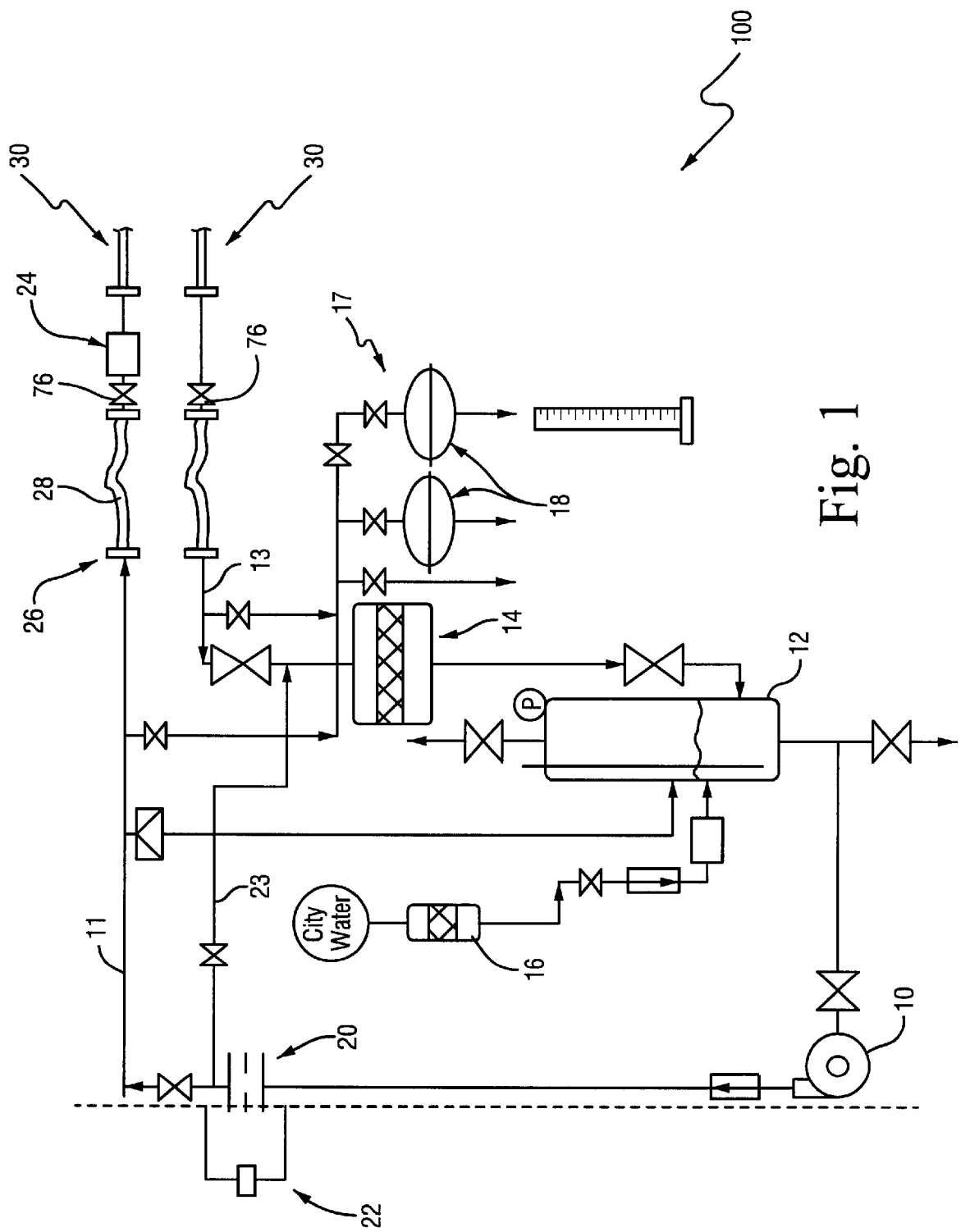
FIGS. 1 and 2 together illustrate a test rig provided as a preferred embodiment of the invention.

The rig of the invention was developed in particular to evaluate the deposition of and to evaluate cleaning processes to remove solid particulate contamination that has either been artificially injected into gas turbine hardware or that has been left within the components as a result of their manufacturing process.

To minimize the potential for oxidation of metallic components being liberated into the test section and adversely affecting results, in the presently preferred embodiment, all components that make up the rig are formed from stainless steel. Thus, with reference to FIG. 1, in a first fluid delivery section 100 of the test rig of the invention, at least one main pump 10, preferably a stainless steel pump, is provided which adapted to achieve $1/60^{th}$ of the gas turbine flow rate into the test section 200. By way of example, the rig may use an 80 gpm 300 psi capable pump. However, the rig can utilize virtually any size rating of water pump, the 80 gpm selection being merely a choice of economics at the time rig hardware was procured in this case.

A stainless steel water reservoir 12 is provided to allow recirculation for long duration testing. Upstream of the water reservoir 12, a filter cartridge 14 is provided, which must employ the same filtration level used in the target power plant fluid delivery system, thus simulating the operation level of particle filtration being cleaned and allowing captured debris to be quantified. Recirculating flow in reservoir 12 can be supplemented as desired with e.g., city water, which also flows via a general filter 16, which prevents gross particles from entering the system. Also included in the illustrated rig is a sampling system 17 including two millipore sampling filters 18 for monitoring, e.g., a particulate content of fluid flowing along a first fluid flow path 11 downstream of the pump 10 and/or for monitoring, e.g., a particulate content of fluid flowing along a second fluid flow path 13 that is recirculating to the pump 10.

A flow rate orifice 20 or other known means to verify flow rate of each test run and a flow rate delta pressure measuring device 22 are provided downstream of the pump 10. Also, a test section start-up bypass line 23 is provided downstream of the flow rate orifice 20 for directing flow to recycle to the reservoir 12 via filter 14 during start-up, to initially flush that part of the fluid delivery section 100, as discussed below.

To simulate solid particles entering the steam delivery system from the power plant piping and equipment, a contamination input port 24 is provided downstream of a flexible coupling generally shown at 26. A two-inch hose 28 is provided as the flexible coupling section in the illustrated embodiment. At point 30, connection is provided to connect to any test section 200 that can hold test component(s), such as assembly or sub-assembly components, or even an arrangement of test sections such as flow visualization studies, pressure drop evaluation, or even proof pressure testing. Thus, connection point 30 contributes to the unique flexibility of this rig design. Also, as described in greater detail below, the flexible coupling 26, 28, 30 allows the orientation of the component or assembly being tested to be changed according to the testing being carried out, thus further contributing to the unique flexibility of the rig of the invention.

Figure 2:
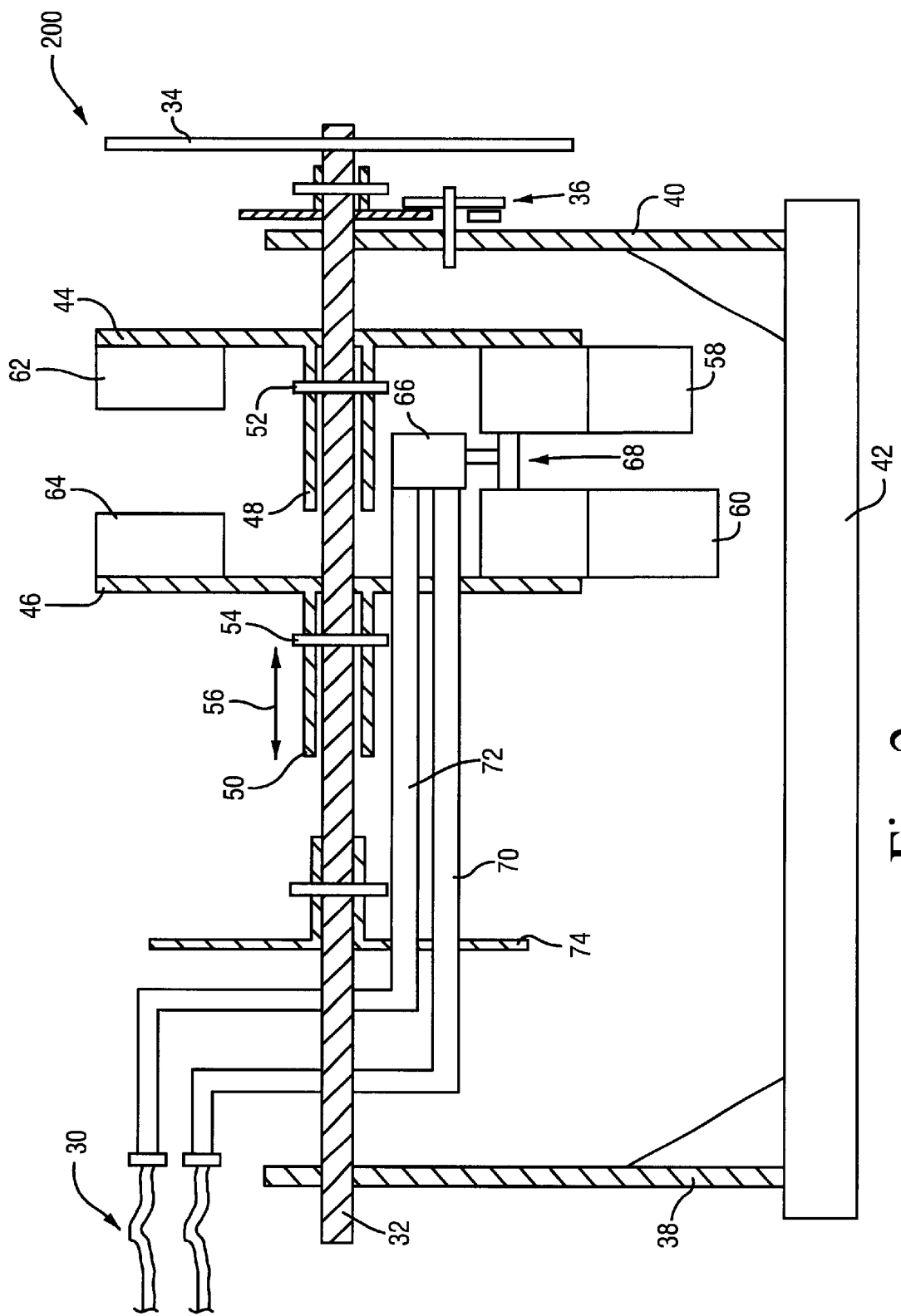

FIG. 2 illustrates an exemplary test section 200 coupled at point 30 to the fluid delivery section 100 of FIG. 1. In the illustrated embodiment, the test section is comprised of an assembly that is adapted to selectively alter the orientation of the test component relative to vertical. Accordingly, the test component is mounted for rotation about a rotary axis defined by pipe shaft 32. A rotation bar 34 is disposed at one end of the pipe shaft in the illustrated embodiment to facilitate orientation of the component in advance of initiating the test procedure. As schematically illustrated at 36, a rotation lock is provided for locking the test assembly at a position prescribed by the rotation bar. In the illustrated embodiment, the pipe shaft 32 is disposed at a height of about 4 feet above the ground and is supported by first and second vertical supports 38,40 that are connected by a base channel 42.

First and second channel arms 44,46 are fixedly mounted to the pipe shaft 32 so that as the pipe shaft is rotated, the channel arms are rotated as well. In the illustrated embodiment, the channel arms each include a cylindrical support pipe 48,50 fixedly secured thereto and projecting axially therefrom in surrounding relation to the pipe shaft 32. The support pipes 48,50 are locked to rotate with the pipe shaft with a suitable set pin or a key bolt 52,54 as illustrated. The disposition of each channel arm along the length of the pipe shaft may be adjusted as shown by arrow 56 by removing the respective key bolt and displacing the channel arm and support pipe assembly along the pipe shaft. Key bolt holes may be defined at spaced locations along the pipe shaft to determine positions for the channel arms. In the illustrated embodiment, a to scale first test article 58 and a to scale second test article 60 are mounted respectively to the first and second channel arms 44,46. Counterweights 62,64 are provided on the diametrically opposite ends of the channel arms to balance the assembly.

A representative manifold system collectively illustrated at 66 is provided for directing flow into and out of the respective component test articles. As noted above, in the presently preferred embodiment, the test section is a $\frac{1}{60}^{th}$ scale simulation of the power plant fluid delivery circuit. Thus, supply and return elbows 68 as well as supply and return tubes and other associated hardware shown generally at 70,72 required to complete the scale simulation of the power plant fluid delivery circuit are provided. In the illustrated embodiment, a support arch 74 for the simulated hardware 70,72 that is rotatably locked with respect to the pipe shaft is further provided to guide the simulated hardware as the components 58,60 being tested are re-oriented relative to horizontal.

The first, fluid delivery section 100 of the test rig will thus sequentially pump water into the test section 200, along a third fluid flow path defined by the axial and radial tubes 70 and the manifold system 66, through the test article 58, and through another test article 60. Next the water is pumped back toward coupling 30 along a fourth fluid flow path defined by the steam outlet manifold 66 and axial and radial tubes 72, at which point the water will be recycled back to reservoir 12 through filter 14 and ultimately to the rig's main pump 10.

As presently proposed, the flush rig test procedure is adapted to conduct 3 primary tests. Test 1 is the system flush. This procedure occurs after the installation of the test article(s) bypass hardware. The main flow system is flushed. Then the sampling system is flushed. Next, the water reservoir is flushed via bypass line 23. Entrapped air is removed through the contamination input port 24 and the rig isolation valves 76 are closed. The system is then ready for the required testing.

The second test is contamination removal. First, the test article(s) are opened and a selected amount of contamination is deposited therein. The test is then repeated with the contaminated test articles positioned in each of the vertical, horizontal and bottom vertical positions according to a repositioning of the rotation arm 34. The full main flow is then established through the contaminated test article(s) and continues for 2 minutes following each repositioning of the test article(s). The filters and test hardware can then be removed and inspected for particulate contamination.

The third test is the contamination injection and removal step. First, clean test article(s) are installed in the test station 200. The test is preferably repeated with the test article(s) positioned in each of the vertical, horizontal and bottom vertical positions. A selected amount of contamination is inserted in the contamination port 24 and the pump 10 and flow are started for a minimum of 2 minutes or until the sampling filters 18 indicate no further contamination is passing through the system. The filter and test hardware can then be removed and inspected. Thus, test number 3 indicates the deposition of contaminant within the test article.

Other test sequences and variations of the tests described above can then be practiced based of the results of tests 2 and 3.

As is apparent from the forgoing, the invention provides a process and assembly evaluating the deposit of debris in and for evaluating the removal of loosely held deposits from critical regions, such as transfer regions, in a power plant fluid delivery system, without disassembling the entire system. In a presently preferred implementation, the test rig of the invention is used to evaluate and flush turbine section hot gas path components such as turbine section airfoils.

While the invention has been described in connection with what is presently considered to be a practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A test rig for evaluating solid particulate contamination disposed in an interior flow passage of a test article, comprising:
   a first, fluid delivery section including:
      at least one fluid pump;
      a fluid reservoir defining a fluid source for said at least one fluid pump;
      a filter cartridge disposed upstream of at least one of said pump and said fluid reservoir for filtering fluid flowing thereto;
      at least one coupling for fluidly coupling said fluid delivery part to a test section;
      a first fluid flow path for conducting fluid from said pump to said at least one coupling; and
      a second fluid flow path for conducting fluid from said at least one coupling to said reservoir; and
   a test section including:
      a test assembly for rotatably supporting at least one test article having an interior flow passage to be evaluated, so that a vertical orientation of said test article can be selectively altered;
      a third fluid flow path for conducting fluid from said at least one coupling to said at least one test article; and
      a fourth fluid flow path for conducting fluid from said at least one test article to said at least one coupling.

2. A test rig as in claim 1, wherein substantially all metallic components of said fluid delivery section in communication with fluid flow therethrough are formed from stainless steel thereby to substantially preclude the liberation of oxidation of said metallic components into the test section.

3. A test rig as in claim 1, wherein said pump is adapted to achieve a prescribed fraction of an in use fluid flow rate through the test article being tested.

4. A test rig as in claim 3, wherein said pump is adapted to provide $\frac{1}{60}^{th}$ of the in use fluid flow rate through the test article.

5. A test rig as in claim 1, further comprising a sampling system for selectively sampling fluid from at least one of said first and second flow paths.

6. A test rig as in claim 5, wherein the sampling system includes at least one sampling filter for filtering said sampled fluid.

7. A test rig as in claim 1, further comprising a sensor for determining a flow rate of fluid flow through said first fluid flow path.

8. A test rig as in claim 7, wherein said sensor comprises a flow rate orifice and a flow rate delta pressure measuring device.

9. A test rig as in claim 1, further comprising a contamination input port adjacent said at least one coupling for adding a contaminant to fluid flowing through said first fluid flow path.

10. A test rig as in claim 1, wherein said at least one coupling comprises at least first and second flexible couplings for respectively coupling said first and third flow paths and said second and fourth flow paths.

11. A test rig as in claim 1, wherein said test assembly includes a shaft defining a rotary axis and a rotation lock for locking the test assembly in a selected rotary orientation.

12. A test rig as in claim 11, wherein said test assembly further includes at least one channel arm, each supporting a respective test article, each said channel arm being fixedly mounted to said shaft so that as the pipe shaft is rotated, the channel arm is rotated.

13. A test rig as in claim 12, wherein a cylindrical support pipe is fixedly secured to each said channel arm and projects axially therefrom in surrounding relation to the shaft, said support pipes being selectively locked to rotate with the shaft and selectively unlocked therefrom for being axially displaced along the shaft.

14. A test rig as in claim 13, including a key bolt for selectively locking and unlocking a respective cylindrical support pipe to said shaft.

15. A test rig as in claim 1, wherein said third and fourth flow paths include a manifold system for directing flow into and out of said test article.

16. A method for evaluating solid particulate contamination disposed in an interior flow passage of a test article, comprising:
   providing a test rig comprising:
      a first, fluid delivery section including:
         at least one fluid pump;
         a fluid reservoir defining a fluid source for said at least one fluid pump;
         a filter cartridge disposed upstream of at least one of said pump and said fluid reservoir for filtering fluid flowing thereto;
         at least one coupling for fluidly coupling said fluid delivery part to a test section;
         a first fluid flow path for conducting fluid from said pump to said at least one coupling; and
         a second fluid flow path for conducting fluid from said at least one coupling to said reservoir; and
      a test section including:
         a test assembly for rotatably supporting at least one test article having an interior flow passage to be evaluated, so that a vertical orientation of said test article can be selectively altered;
         a third fluid flow path for conducting fluid from said at least one coupling to said at least one test article; and
         a fourth fluid flow path for conducting fluid from said at least one test article to said at least one coupling;
   installing a clean test article in said test assembly, in fluid communication with each of said third and forth flow paths;
   depositing a selected amount of contamination in at least one selected portion of said test article;
   orienting said test assembly so that said test article is disposed in a vertical position;
   actuating said at least one pump to a prescribed flow rate and flowing fluid through said fluid delivery section and said test section for a prescribed period; and
   examining said filter to determine an amount of contamination removed from said test article by said fluid flow.

17. A method as in claim 16, further comprising orienting said test assembly so that said test article is disposed in a horizontal position and repeating said actuating and examining steps.

18. A method as in claim 16, further comprising orienting said test assembly so that said test article is disposed in a bottom vertical position and repeating said actuating and examining steps.

19. A method as in claim 16, wherein said at least one coupling is a flexible coupling whereby an orientation of said test assembly can be modified without decoupling said at least one coupling.

20. A method for evaluating solid particulate contamination disposed in an interior flow passage of a test article, comprising:

providing a test rig comprising:

a first, fluid delivery section including:

at least one fluid pump;

a fluid reservoir defining a fluid source for said at least one fluid pump;

a filter cartridge disposed upstream of at least one of said pump and said fluid reservoir for filtering fluid flowing thereto;

at least one coupling for fluidly coupling said fluid delivery part to a test section;

a first fluid flow path for conducting fluid from said pump to said at least one coupling;

a contamination input port adjacent said at least one coupling for adding a contaminant to fluid flowing through said first fluid flow path; and a second fluid flow path for conducting fluid from said at least one coupling to said reservoir; and a test section including:

a test assembly for rotatably supporting at least one test article having an interior flow passage to be evaluated, so that a vertical orientation of said test article can be selectively altered;

a third fluid flow path for conducting fluid from said at least one coupling to said at least one test article; and a fourth fluid flow path for conducting fluid from said at least one test article to said at least one coupling;

installing a clean test article in said test assembly, in fluid communication with each of said third and forth flow paths;

orienting said test assembly so that said test article is disposed in a vertical position;

depositing a selected amount of contamination into said contamination input port;

actuating said at least one pump to a prescribed flow rate and flowing fluid through said fluid delivery section and said test section for a prescribed period; and examining said filter and said test article to determine an amount and location of contamination deposited therein.

21. A method as in claim 20, further comprising orienting said test assembly so that said test article is disposed in a horizontal position and repeating said actuating and examining steps.

22. A method as in claim 20, further comprising orienting said test assembly so that said test article is disposed in a bottom vertical position and repeating said actuating and examining steps.

23. A method as in claim 20, wherein said at least one coupling is a flexible coupling whereby an orientation of said test assembly can be modified without decoupling said at least one coupling.

* * * * *

UNITED STATES PATENT AND TRADEMARK OFFICE
CERTIFICATE OF CORRECTION

PATENT NO. : 6,422,068 B1
DATED : July 23, 2002
INVENTOR(S) : Schroder et al.

It is certified that error appears in the above-identified patent and that said Letters Patent is hereby corrected as shown below:

Column 2,
Line 31, "1/6$^{th}$" should be -- 1/60$^{th}$ --.

Signed and Sealed this

Twenty-sixth Day of November, 2002

Attest:

Attesting Officer

JAMES E. ROGAN
Director of the United States Patent and Trademark Office